US009733463B2

(12) United States Patent
Eslami et al.

(10) Patent No.: US 9,733,463 B2
(45) Date of Patent: Aug. 15, 2017

(54) SURGERY SYSTEM

(71) Applicant: Carl Zeiss Meditec AG, Jena (DE)

(72) Inventors: Abouzar Eslami, München (DE); Corinna Maier-Matic, Neuried (DE)

(73) Assignee: CARL ZEISS MEDITEC AG, Jena (DE)

(*) Notice: Subject to any disclaimer, the term of this patent is extended or adjusted under 35 U.S.C. 154(b) by 142 days.

(21) Appl. No.: 14/722,233

(22) Filed: May 27, 2015

(65) Prior Publication Data

US 2015/0342698 A1   Dec. 3, 2015

(30) Foreign Application Priority Data

May 27, 2014   (DE) .......................... 10 2014 007 908

(51) Int. Cl.
| | |
|---|---|
| *G02B 21/22* | (2006.01) |
| *A61F 9/007* | (2006.01) |
| *A61B 90/00* | (2016.01) |
| *A61B 90/20* | (2016.01) |
| *G02B 21/00* | (2006.01) |

(Continued)

(52) U.S. Cl.
CPC .............. *G02B 21/22* (2013.01); *A61B 34/25* (2016.02); *A61B 90/20* (2016.02); *A61B 90/361* (2016.02); *A61F 9/00727* (2013.01); *G02B 21/0012* (2013.01); *A61B 2034/2065* (2016.02); *A61B 2034/256* (2016.02); *A61B 2090/364* (2016.02);

(Continued)

(58) Field of Classification Search
CPC .... G02B 21/0012; G02B 21/22; A61B 34/25; A61B 90/20; A61B 90/361; A61B 3/00; A61B 3/1173; A61F 9/00727

USPC ........................................................ 606/5

See application file for complete search history.

(56) References Cited

U.S. PATENT DOCUMENTS

| | | | |
|---|---|---|---|
| 7,774,155 B2 | 8/2010 | Sato et al. | |
| 8,311,791 B1 * | 11/2012 | Avisar ................... | G09B 23/28 702/19 |

(Continued)

FOREIGN PATENT DOCUMENTS

| | | |
|---|---|---|
| CN | 103110475 A | 5/2013 |
| DE | 10 2011 015 149 A1 | 9/2012 |

(Continued)

OTHER PUBLICATIONS

Extended European Search Report issued in corresponding European application No. 15 001 594.9 dated Oct. 20, 2015.

(Continued)

*Primary Examiner* — Christopher A Flory

(74) *Attorney, Agent, or Firm* — Patent Portfolio Builders PLLC

(57) ABSTRACT

A surgery system comprises a camera obtaining camera images, an OCT system, a data memory storing geometry data of a surgical tool 133 and a controller configured to identify a first portion of the tool in the camera images by object recognition using the geometry data; to determine, in the field of view, first locations where the tool is located and second locations aside of the tool; to trigger the OCT system to perform depth scans at the first and second locations; to identify a second portion 153 of the tool in the depth scans by object recognition using the geometry data; and to generate a first image 154 representing a third portion 157 of the tool based on the geometry data and the depth scans.

19 Claims, 5 Drawing Sheets

(51) Int. Cl.
*A61B 34/00* (2016.01)
*A61B 34/20* (2016.01)

(52) U.S. Cl.
CPC . *A61B 2090/365* (2016.02); *A61B 2090/3618* (2016.02); *A61B 2090/3735* (2016.02)

(56) References Cited

U.S. PATENT DOCUMENTS

| | | | |
|---|---|---|---|
| 8,848,203 B2* | 9/2014 | Bridges | G01C 15/002 356/614 |
| 8,880,151 B1* | 11/2014 | Stolka | A61B 19/5244 600/424 |
| 9,041,914 B2* | 5/2015 | Tohme | G01S 17/003 356/3.01 |
| 2010/0268067 A1* | 10/2010 | Razzaque | A61B 8/4245 600/424 |
| 2011/0018871 A1* | 1/2011 | Shirahata | A61B 8/00 345/419 |
| 2011/0106102 A1 | 5/2011 | Balicki et al. | |
| 2011/0137156 A1* | 6/2011 | Razzaque | A61B 34/20 600/424 |
| 2011/0164064 A1* | 7/2011 | Tanaka | A61B 5/1075 345/667 |
| 2012/0007839 A1 | 1/2012 | Tsao et al. | |
| 2012/0022408 A1 | 1/2012 | Hubschman et al. | |
| 2012/0101370 A1* | 4/2012 | Razzaque | A61B 34/20 600/424 |
| 2012/0184846 A1 | 7/2012 | Izatt et al. | |
| 2013/0123759 A1 | 5/2013 | Kang et al. | |
| 2013/0190734 A1 | 7/2013 | Taylor et al. | |
| 2013/0218269 A1 | 8/2013 | Schachar et al. | |
| 2013/0230837 A1 | 9/2013 | Meglan et al. | |
| 2013/0267776 A1 | 10/2013 | Brennan et al. | |
| 2013/0322108 A1 | 12/2013 | Mansour | |
| 2014/0024949 A1 | 1/2014 | Wei et al. | |
| 2014/0142426 A1* | 5/2014 | Razzaque | A61B 34/20 600/424 |
| 2014/0142591 A1* | 5/2014 | Alvarez | A61F 9/00736 606/130 |
| 2014/0221822 A1 | 8/2014 | Ehlers et al. | |
| 2015/0190038 A1* | 7/2015 | Sakuragi | A61B 1/00009 348/45 |
| 2015/0193966 A1* | 7/2015 | Sakuragi | G06T 19/20 348/46 |

FOREIGN PATENT DOCUMENTS

| | | |
|---|---|---|
| WO | 2012/012540 A2 | 1/2012 |
| WO | 2012/012565 A2 | 1/2012 |
| WO | 2012/100030 A2 | 7/2012 |
| WO | 2012/130449 A1 | 10/2012 |
| WO | 2014/121268 A1 | 8/2014 |

OTHER PUBLICATIONS

Richa, R. et al., "Vision-based Proximity Detection in Retinal Surgery," IEEE Transactions on Biomedical Engineering, vol. 59, Issue 8, Jun. 5, 2012, pp. 2291-2301, IEEE, ISSN: 0018-9294; doi: 10.1109/TBME.2012.2202903.

Hattenbach, L.O. et al., "Experimental Endoscopic Endovascular Cannulation: A Novel Approach to Thrombolysis in Retinal Vessel Occlusion," Investigative Ophthalmology Visual Science, vol. 53, No. 1, Jan. 2012, pp. 42-46.

Yang, S. et al., "Optical Coherence Tomography Scanning with a Handheld Vitreoretinal Micromanipulator," 2012 Annual Conference of the Engineering in Medicine and Biology Society, Aug. 28-Sep. 1, 2012, San Diego, CA, pp. 948-951, Print ISBN: 978-1-4244-4119-8, doi: 10.1109/EMBC.2012.6346089.

Steady-Hand Eye Robot; (https://ciis.lcsr.jhu.edu/dokuwiki/doku.php?id=research.eyerobots).

German Office Action, with translation thereof, issued on corresponding DE application No. 10 2014 007 908.2, dated Dec. 10, 2014.

* cited by examiner

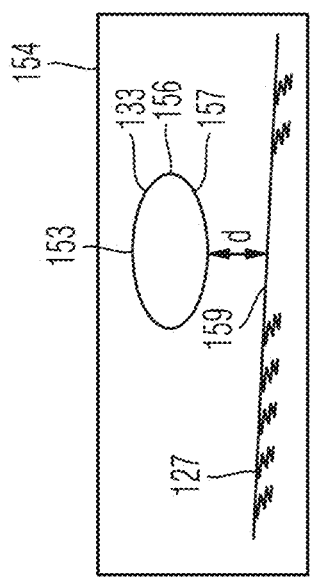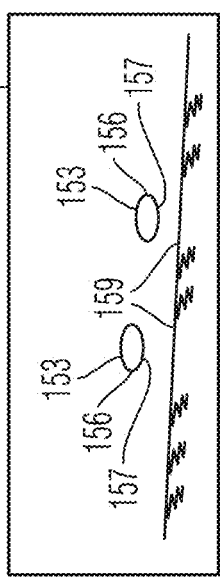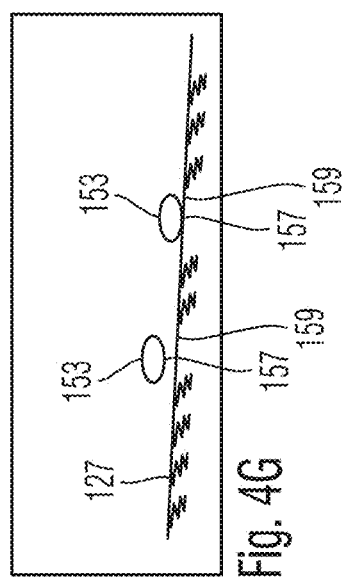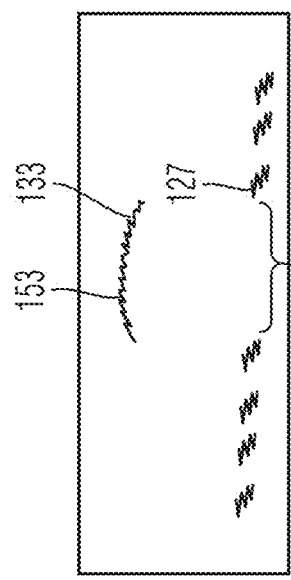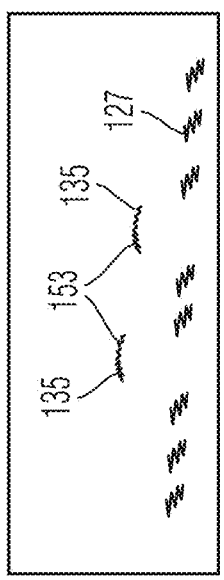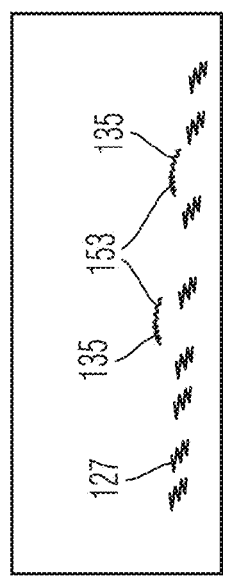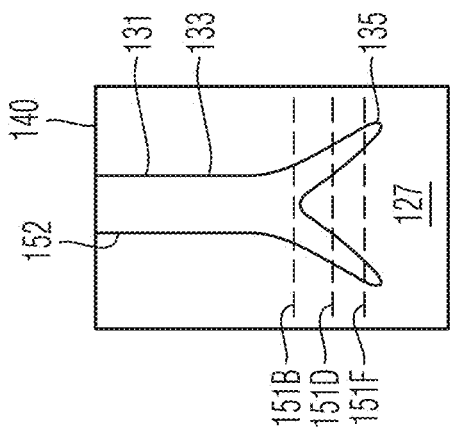

SURGERY SYSTEM

CROSS-REFERENCES TO RELATED APPLICATIONS

The present application claims priority of Patent Application No. 10 2014 007 908.2, filed May 27, 2014 in Germany, the entire contents of which are incorporated by reference herein.

FIELD

The present invention relates to surgery systems assisting the usage of surgical tools during microsurgical interventions.

BACKGROUND

During such interventions, a surgeon holds the tool with the hand, for example, and moves the tool relative to the tissue to be treated in order to perform manipulations on the tissue. These movements and manipulations are performed under visual supervision. For assisting the visual supervision, the surgery systems provide a microscope, for example. The microscope generates an image of the tissue to be treated and the tool in a top view. It is difficult for the surgeon to estimate the distance from the tool to the tissue. Sensitive tissue may be damaged when unintentionally touched and/or pressure is applied to the tissue by the tool. An example for such an intervention are surgeries on the retina of an eye which are performed with help of a surgery microscope having an integrated OCT system. The OCT system allows to generate cross-sectional images of the tissue layers of the retina and to identify regions to be treated within these images. In this case, the movements with the tool necessary for the treatment are performed by the surgeon under visual supervision using the surgery microscope by viewing into the oculars of the surgery microscope.

It has already been proposed to perform an approach of the surgical tool to the tissue to be treated not only under the visual supervision, which is possible by means of the microscope image, but also by accounting for the images generated by the OCT system. However, this is problematic as tools are badly visible in OCT images and tissue regions disposed in the beam path of the OCT system behind the tool are shadowed so that it is also difficult to estimate the distance between the tool and the tissue layers from the OCT images. Furthermore, OCT scans of large object areas, where the tool may be located eventually, require relatively much time so that representations of the tool and the tissue regions cannot be obtained from OCT scans in real-time in a satisfactory manner.

SUMMARY

It is an object of the present invention to provide a surgery system which assists the handling of a surgical tool relative to tissue regions to be treated, wherein the handling of the surgical tool is performed by a surgeon.

According to embodiments, a surgery system is suggested, wherein the surgery system comprises an OCT system and a camera having optics. The optics are configured to image a field of view onto the camera so that the camera may obtain two-dimensional camera images of the field of view and may generate data representing the camera images. The tissue region to be treated may be disposed in the field of view and the surgeon may move the surgical tool to the tissue region so that the tissue region and the tool are disposed in the field of view and contained in the camera images. The surgeon may perform the movements of the tool under visual supervision by observing the camera images.

According to exemplary embodiments, the optics are magnifying optics so that the camera and the optics function as a microscope. According to exemplary embodiments herein, the optics comprise at least one ocular and are configured to image at least a portion of the field of view via the ocular so that the surgeon may perform the visual supervision by viewing into the ocular.

The OCT system is configured to perform depth scans at selectable locations contained in the field of view and to generate data representing the depth scans. The OCT system works according to the principle of the optical coherence tomography and detects light which is backscattered from the selected locations in dependence of the tissue depth. In the terminology used in the context of optical coherence tomography, such a depth scan is also referred to as an A-scan. The OCT system may work according to different principles. According to exemplary embodiments, the backscattered light is detected from different depths one after another in time. This principle is also referred to as Time-Domain-OCT. According to other exemplary embodiments, the light is detected from the different depths in dependence of the optical wave number. This principle is also referred to as Fourier-Domain-OCT.

According to exemplary embodiments herein, the interfering light is directed onto a line detector via a dispersive spectrometer and is detected by the line detector. This kind of Fourier-Domain-OCT is conventionally referred to as Spectral-Domain-OCT. According to another exemplary embodiment herein, the OCT measurement light is generated by a narrow-band light source, the wavelength of light emitted by the light source may be varied quickly and the light is detected in dependence of the set wavelength. This principle is conventionally referred to as Optical-Frequency-Domain-OCT or Swept-Source-OCT. However, the present invention and embodiments are not limited to any of the above mentioned OCT principles.

The surgery system further comprises a data memory storing geometry data of at least one surgical tool. In particular, the geometry data of the tools, which are to be used during a planned surgical intervention, are stored in the data memory. The geometry data are stored in the data memory for the purpose of automatically identifying a specific tool currently in use in the camera images and in the depth scans by object recognition. The geometry data represent the geometry of the respective surgical tool. For example, these data represent the physical extent, such as length and width, and an orientation of surfaces of the tool at different locations of the tool. For example, the geometry data may be CAD-data which may have been generated in the process of construction of the tool using a computer-aided-design (CAD)-tool. The geometry data may be stored in the data memory prior to the intervention, and in particular prior to the obtaining of camera images by the camera.

According to exemplary embodiments, the surgical tool is a needle, a cutter, a scraper, tweezers or the like.

The surgery system further comprises a controller receiving the data from the camera and processing the camera images represented by these data. The controller may comprise one or multiple components. Each of the components may comprise one or multiple electronic circuits, each of which may also work as a computer, i. e. may comprise working memory and one or multiple processors which may access the working memory and may execute software modules stored in the working memory in order to process data. The components of the controller may be distributed among multiple locations and be connected with each other by control wires, data wires and data networks. The functionality of the controller may be implemented by analog electronics, digital electronics, software modules and combinations thereof.

The controller further receives the data generated by the OCT system and may process the depth scans represented these data.

Furthermore, the controller is configured to identify a first portion of the at least one tool in the camera images by object recognition using the geometry data of the at least one surgical tool. Identifying may imply that the tool present in the camera images may be identified among a set of predetermined tools. That is, the tool present in the camera images may be distinguished from the other tools of set of predetermined tools. Therefore, by object recognition, the controller may determine which one of at least one predetermined tool is present in the camera images.

The controller determines first locations in the field of view where the tool is located as well as second locations in the field of view aside of the tool. In particular, the controller may be configured to determine the first and second locations based on at the camera images and/or depth scans.

Furthermore, the controller is configured to trigger the OCT system to perform depth scans at each of the determined first locations and the determined second locations. According to exemplary embodiments, the first and second locations are disposed on a line in the field of view, in particular a straight line, and are equidistantly disposed from each other. Then, the OCT system obtains a plurality of depth scans at the locations disposed on the line. In the terminology used in the context of optical coherence tomography, such a scan is also referred to as B-scan. The data obtained in such a scan represent a sectional image of an object, gathered by backscattered light. The tool is contained in this sectional image and may be identified therein. If any tissue to be treated is also contained in the sectional image, a distance between the tool and the surface of the tissue to be treated may be deduced by observing the image. However, by observing the image of the B-scan, this may not be possible to a satisfactory degree at all times as a surface of the tool shadows other portions of the tool and the tissue regions disposed in the beam path of the OCT system behind this surface.

According to further exemplary embodiments, the first locations and the second locations are disposed on multiple lines, in particular straight lines, disposed at a distance from each other in the field of view so that the OCT system obtains a series of B-scans. In the terminology used in the context of optical coherence tomography, such a scan is referred to as C-scan.

According to exemplary embodiments, the at least one surgical tool has a long axis and the one or multiple lines, along which the first and second locations are disposed, are oriented in a way that the lines are orientated parallel to the long axis or orthogonal to the long axis. The images represented by the B-scans then contain the tool in a manner which is simply comprehensible for humans so that the surgeon may supervise the movement of the tool based thereon.

However, the first and second locations do not need to be disposed on a (straight) line. In particular, every other selection of locations is possible so that scan strategies different from the traditional B-scans may be selected as well.

According to further exemplary embodiments, the tool has a distal end located in the field of view and the controller triggers the OCT system to perform the depth scans at third locations where the distal end of the tool is located in the field of view at a greater rate, i. e. using a greater frequency per unit time, compared to other locations located at a distance from the distal end. Herein, it is assumed that touching of the tissue by the tool and, therefore, unintended damaging of the tissue by the tool occur with the distal end of the tool. By performing the A-scans at the distal end of the tool using a greater rate, unintentional approaches of the tool to the tissue may be detected quicker and at a greater accuracy.

According to exemplary embodiments, the controller is further configured to identify a second portion of the at least one surgical tool in the depth scans by object recognition using the geometry data of the at least one surgical tool. This object recognition may be simplified because the tool in question was already identified by the object recognition in the camera images and because an expected position and orientation of the tool relative to the depth scans is already known from the object recognition in the camera images and the selection of the first and second locations based thereon.

After the object recognition of the tool in the depth scans, the controller generates a first image representing at least one third portion of the at least one surgical tool, wherein the representation of the at least one third portion of the at least one surgical tool is based on the geometry data and wherein a position of this representation of the at least one third portion of the at least one surgical tool in the generated first image is based on the depth scans. The third portion of the tool may overlap the portion of the tool identified by the object recognition in the depth scans, but may also be different from it.

According to exemplary embodiments, the at least one third portion of the at least one surgical tool is unidentifiable in the depth scans or just badly identifiable in the depth scans. Accordingly, the third portion of the tool may comprise, for example, such portions of the tool which are shadowed in the beam path of the OCT system during the depth scans and are, therefore, unidentifiable in the depth scans or just badly identifiable in the depth scans. During a surgical intervention, such portions of the tool are for the most part also those portions of the tool which are located closest to the tissue to be manipulated and also may potentially harm this tissue. According to exemplary embodiments, the generated first image also represents the depth scans. Accordingly, such portions of the tool, which themselves are unidentifiable in the depth scans, as well as the depth scans are represented in the generated first image. If the depth scans are performed as B-scans, for example, the second portion of the tool identifiable in the B-scan, the tissue to be manipulated and the third portion of the tool unidentifiable in the depth scans are visible in a representation of the generated first image. Therefore, the controller has "complemented" the representation of the tool in the generated first image so that the surgeon can visually supervise an approach of the tool to the tissue to be manipulated by the generated first image at a high accuracy.

According to exemplary embodiments, the generated first image further represents the second portion of the at least one surgical tool, wherein the representation of the second portion of the at least one surgical tool is based on the geometry data and wherein a position of the representation of the second portion of the at least one surgical tool in the generated first image is based on the depth scans. Therefore, the generated first image contains a representation of the second portion and the third portion of the tool wherein the second portion of the tool would be identifiable in the depth scans and, therefore, would also be perceivable by the surgeon by observing the first image. However, the representation may be generated more precisely based on the geometry data as a representation based on the depth scans alone may be blurred and be low-contrast due to measurement inaccuracies such as noise.

According to exemplary embodiments, the second portion and/or the at least one third portion of the at least one surgical tool are represented in the generated first image by colors being different from these colors used to represent the depth scans in the generated first image. For example, the depth scans may be illustrated in a conventional fashion as grey to light-grey intensity values on black background, whereas the second portion and/or the third portion of the tool may be illustrated in red or green color.

According to further exemplary embodiments, the data memory further stores geometry data of at least one anatomic structure and the controller is further configured to identify a first portion of the at least one anatomic structure in the depth scans by object recognition using the geometry data of the at least one anatomic structure. The generated first image then may represent at least one second portion of the anatomic structure, wherein the representation of the at least one second portion of the anatomic structure is based on the geometry data of the at least one anatomic structure and wherein a position of the representation of the at least one second portion of the at least one anatomic structure in the generated first image is based on the depth scans. In the context of a surgical intervention on the retina of an eye, the geometry data of the anatomic structure may comprise geometry data of different tissue layers of a typical retina of an eye. However, it is also possible that these geometry data are based on previously obtained OCT scans of the tissue region to be manipulated. As previously described with reference to the representation of the second portion of the surgical tool in the generated first image, the anatomic structure may be perceived more clearly by the surgeon by observing the generated first image as the representation of the anatomic structure in the generated first image is based on the geometry data. Also herein, the anatomic structure may be represented in the generated first image by colors being different from those colors used to represent the depth scans in the generated first image.

The representation of the anatomic structure based on the geometry data may also provide the advantage that the anatomic structure may be perceivable in such portions of the generated first image where shadowing occurred in the OCT scan due to the surgical tool being disposed in the beam path before the anatomic structure. In this case, the controller also complements the representation of the anatomic structure.

According to exemplary embodiments, the surgery system comprises a user interface, in particular comprising a display on which the controller displays the generated first image. Then, a surgeon may perform the manipulation of the tissue using the tool under visual supervision by observing the display and perceiving the generated first image displayed thereon. If the depth scans were obtained as B-scans, the displayed image represents a cross-section through the tissue layers and the tool disposed before them, wherein the distance between the tool and the surface of the tissue layers may be estimated well as the representation of the tool and the representation of the tissue layers were complemented in the image by the controller.

According to exemplary embodiments, the controller is further configured to generate a second image representing the camera image and the first portion and/or the second portion and/or the at least one third portion of the at least one surgical tool so that the camera image is also improved by complementing or highlighting the tool.

Further embodiments are directed to a method of operating a surgery system.

According to exemplary embodiments, a method of operating a surgery system, in particular a surgery system according to one of the embodiments described herein, comprises storing geometry data of at least one surgical tool; imaging a field of view onto a camera; obtaining two-dimensional camera images of the field of view and generating camera image data representing the camera images; identifying a first portion of the at least one surgical tool in the camera images by object recognition using the geometry data of the at least one surgical tool; determining first locations and second locations in the field of view, wherein the at least one surgical tool is located at the first locations and wherein the second locations are located aside of the at least one surgical tool; performing first depth scans at the determined first and second locations using an OCT system; identifying a second portion of the at least one surgical tool in the first depth scans by object recognition using the geometry data of the at least one surgical tool; generating a first image representing at least one third portion of the at least one surgical tool, wherein the representation of the at least one third portion of the at least one surgical tool is based on the geometry data and wherein a position of the representation of the at least one third portion of the at least one surgical tool in the generated first image is based on the first depth scans. The geometry data of at least one surgical tool may be stored prior to the identifying of the first portion of the at least one surgical tool in the camera images.

According to further exemplary embodiments, the at least one third portion of the at least one surgical tool is unidentifiable in the first depth scans.

According to further exemplary embodiments, the method further comprises determining the first and second locations based on at least one of the camera images and second depth scans.

According to further exemplary embodiments, the generated first image further represents the second portion of the at least one surgical tool, wherein the representation of the second portion of the at least one surgical tool is based on the geometry data and wherein a position of the representation of the second portion of the at least one surgical tool in the generated first image is based on the first depth scans. The generated first image may further represent the first depth scans.

According to further exemplary embodiments, the method further comprises storing geometry data of at least one anatomic structure; identifying a first portion of the at least one anatomic structure in the depths scans by object recognition using the geometry data of the at least one anatomic structure; and wherein the generated first image further represents at least one second portion of the at least one anatomic structure, wherein the representation of the at least one second portion of the at least one anatomic structure is based on the geometry data of the at least one anatomic structure and wherein a position of the representation of the at least one second portion of the at least one anatomic structure in the generated first image is based on the first depth scans. The geometry data of at least one anatomic structure may be stored prior to the identifying of the first portion of the at least one anatomic structure in the depths scans.

According to further exemplary embodiments, the at least one surgical tool has a distal end, and the first locations comprise third locations where the distal end of the at least one surgical tool is located. Herein, the first depth scans may be performed at the third locations at a greater rate compared to those performed at locations which are located at a distance from the distal end of the at least one surgical tool in the field of view.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

FIGS. 4A-4G show schematic illustrations corresponding to the images shown in FIGS. 3A-3G.

DETAILED DESCRIPTION OF EXEMPLARY EMBODIMENTS

Figure 1:
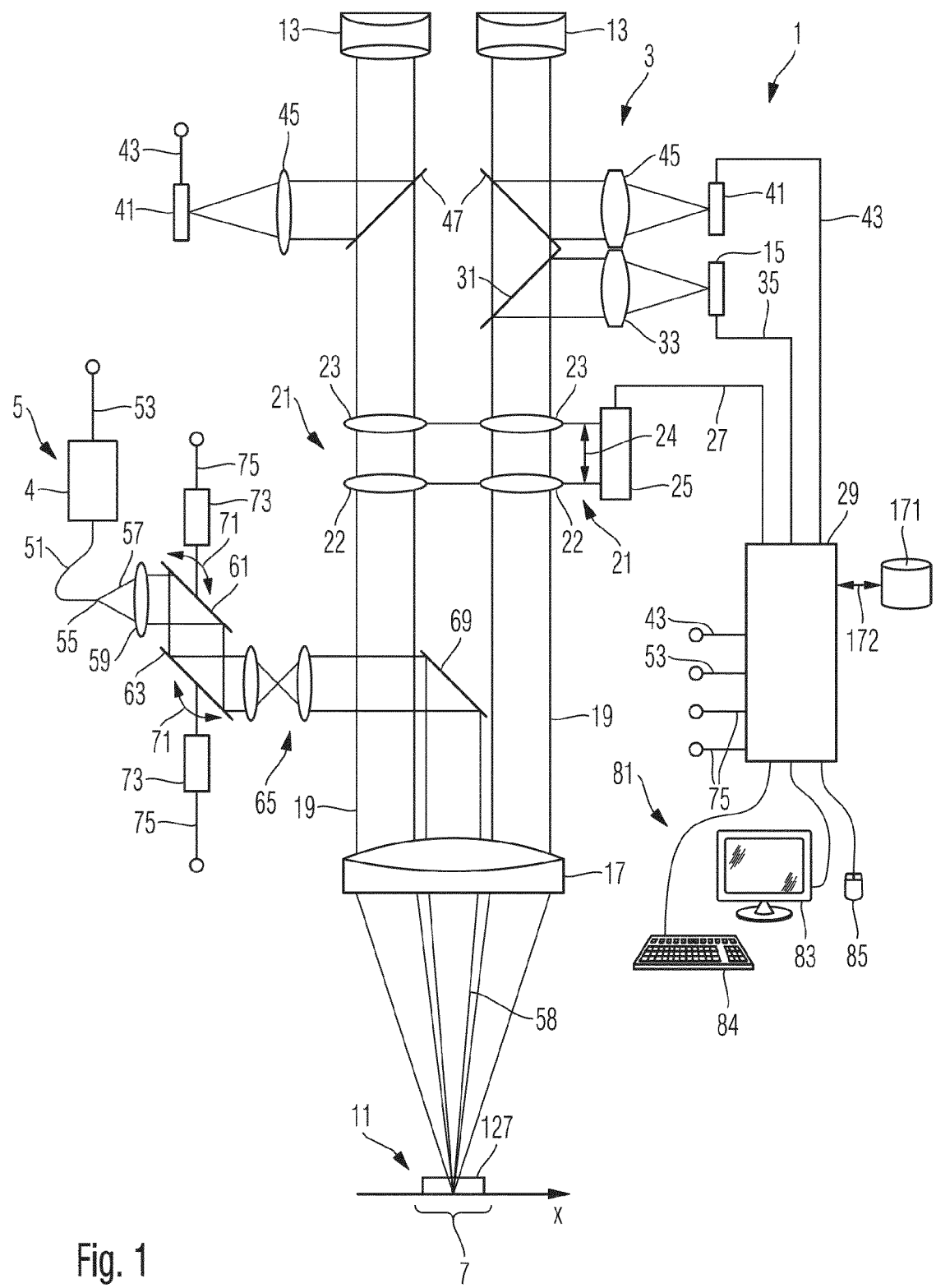
FIG. 1 shows a schematic illustration of an embodiment of a surgery system.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

FIG. 1 is a schematic illustration of a surgery system 1. The surgery system 1 comprises imaging optics 3 configured to generate images of a field of view 7 located within an object region 11. The imaging of the field of view 7 using the imaging optics 3 of the illustrated exemplary embodiment is performed via a pair of oculars 13 into which a surgeon may view with both his eyes. Furthermore, the field of view 7 is imaged onto a camera 15 obtaining images of the field of view 7 and generating data representing the images.

For this, the optics 3 comprise an objective lens 17 which may comprise one or multiple lens elements and which, in accordance with the illustrated example, may image the field of view to infinity. In the beam path behind the objective lens 17, each of two beam bundles 19 is guided through a zoom lens assembly 21 capable of changing an imaging scale of the optics. For this, the two zoom lens assemblies 21 each comprise at least two groups of lenses 22 and 23 displaceable relative to each other in beam direction of the beam bundles 19 as indicated by an arrow 24 in FIG. 1. The displacement of the two groups of lenses 22 and 23 relative to each other is controlled by an actuator 25 which in turn is controlled by a controller 29 via a control wire 27 for setting the imaging scale of the optics 3.

Behind the zoom lens assembly 21, the beam bundles 19 enter the oculars 13. However, a portion of the light of the right one of the beam bundles 19 illustrated in FIG. 1 is redirected by a partially transparent mirror 31 and is directed onto the camera 15 by camera adapter optics 33 so that the camera can detect an image of the field of view 7 of the object region 11. The data generated by the camera 15 are transmitted to the controller 29 via a data wire 35.

The optics 3 further comprise two electronic image displays 41 fed with image data by the controller 29 via a data wire 43. The images displayed by the image displays 41 are each projected into the beam path towards the oculars 13 by projecting optics 45 and a partially transparent mirror 47 disposed in the beam bundle 19 so that a user viewing into the oculars 13 may perceive the images displayed by the displays 41 in superposition with the image of the field of view 7 of the object region 11.

The surgery system 1 further comprises an OCT system 5 for performing OCT measurements. The OCT system 5 comprises an OCT device 4 having an appropriate light source of short coherence and an interferometer, both not illustrated in FIG. 1, wherein OCT measurement light is emitted from the OCT device 4 via a light guiding fiber 51 so that the measurement light may be incident onto an object to be measured and measurement light returning from the object may re-enter the fiber so that the OCT device 4 may examine this returning measurement light and output data representing the measurement. In particular, the OCT device 4 may perform a depth scan also referred to as A-scan, the data of which represent intensities of backscattered measurement light in dependence of the depth. The OCT device 4 is controlled by the controller 29 via a control and data wire 53. The controller 29 also receives the measurement data generated by the OCT system 5 via this wire 53.

The OCT system 5 further comprises collimation optics 59 collimating OCT measurement light 57 emitted from an end 55 of the fiber 51 into a measurement light beam 58. The measurement light beam 58 is deflected at two deflecting mirrors 61 and 63, propagates through projecting optics 65, is incident onto a mirror 69 and is directed by the mirror 69 through the objective lens 17 onto the object region 11. An object 127 (e.g., a tissue such as a retina of an eye) may be disposed in the object region 11 which backscatters OCT measurement light so that the measurement light backscattered by the object 127 propagates along the reverse path through the objective lens 17, the projecting optics 65 and the collimating optics 59 so that at least a portion of this light is coupled into the fiber 51 and arrives at the OCT device 4 where it is examined using the interferometer.

The mirrors 61 and 63 are tiltably disposed in order to deflect the OCT measurement light beam so that the OCT measurement light beam may be incident onto selectable locations within the field of view 7 by setting tilt settings of the mirrors 61 and 63. The tiltability of the mirrors 61 and 63 is indicated by arrows 71 in FIG. 1. The tilt setting of the mirrors 61 and 63 is set by actuators 73 controlled by the controller 29 via control wires 75. Therefore, by driving the actuators 73, the controller 29 may select the location of the object region 11 onto which the OCT measurement light beam is incident.

The controller 29 further comprises a user interface comprising a monitor 83 as an illustrating medium, and a keyboard 84 and a mouse 85 as input media. The user interface also comprises the displays 41 for coupling images generated by the controller 29 into the beam paths to the oculars 13.

In the exemplary embodiment described herein, the surgery system is used to assist a microsurgical intervention on a tissue using a surgical tool.

Figure 2:
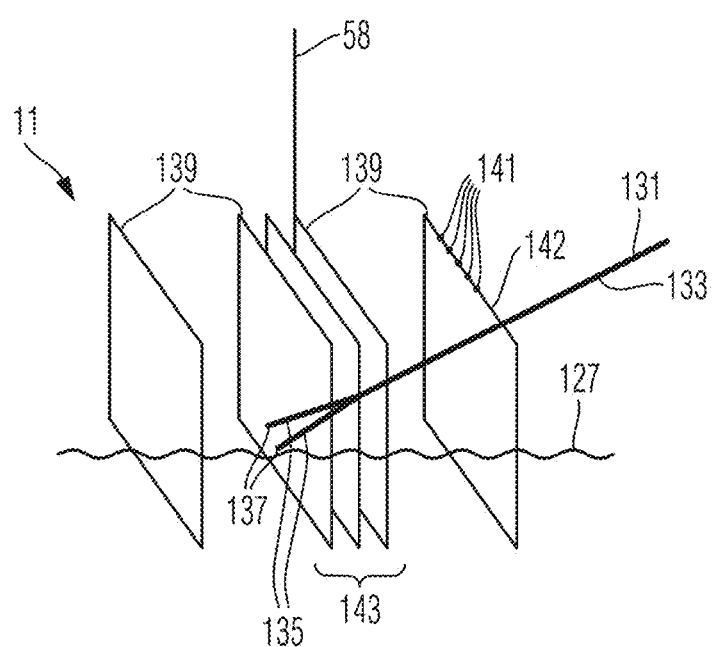
FIG. 2 shows a schematic illustration of an object region of the surgery system of FIG. 1.

FIG. 2 schematically shows such a situation. Therein, the surgical tool has the numeral 131 and has a shaft 133 at which front end a pair of tweezer-like grippers 135 are located, each having a distal end 137. The tool 131 may be used to manipulate the tissue (object 1271 which may be very sensitive. Therefore, unintentional touches of the tissue and an application of pressure to this tissue should be avoided. The surgery system 1 provides a possibility of visual supervision when approaching the tissue 127 with the tool 131.

In the example illustrated below, the tissue (object 127) is the retina of an eye.

The process of approaching the tool 131 to the retina within the field of view 7 may be visually observed by the surgeon in that the surgeon views into the oculars 13 and observes the image of the field of view 7. It is also possible that the surgeon or his assistant observe the image of the field of view 7 on the monitor 83 when the controller 29 displays the image of the field of view 7 detected by the camera 15 thereon. In addition, said image may also be displayed using head mounted display devices.

However, it is difficult to estimate the distance between the tool 131 and the surface of the retina in particular, the distance from the distal ends 137 to the surface of the retina by observing the images of the field of view 7 obtained by the optics 3 as the image represents a top view onto the surface of the retina while the tool 131 is disposed before the retina.

Therefore, the controller 29 triggers the OCT system 5 to perform measurements along sections containing portions of the tool 131 and portions of the retina. In particular, the controller may trigger the OCT system to perform one or multiple B-scans. FIG. 2 shows some exemplary areas 139 in which B-scans are performed. For performing a B-scan, the OCT measurement light beam 58 is directed to a plurality of locations 141 one after another, wherein the locations are disposed along a straight line 142. At each of the locations 141, a depth scan (A-scan) is performed. The data representing the depth scans are transmitted from the OCT system 5 to the controller 29.

The position and the orientation of the areas 139, in which the B-scans are performed, are determined by the controller by analyzing the images of the field of view 7 obtained by the camera 15. For this, the controller 29 performs object recognition in order to identify the tool 131 in the camera images and to determine the position and the orientation of the tool 131 relative to the object region 11 and the field of view 7. Then, the locations 141, where depth scans are performed, are determined and, in particular, determined so that depth scans are performed at locations 141 where the tool 131 is located in the field of view as well as at locations 141 where the tool 131 is not located in the field of view. Therefore, some of the performed depth scans contain the tool and other depth scans do not contain the tool. Herein, the depth scans may be performed at a higher spatial density and/or at a higher rate in the region where the distal ends 137 of the tool 131 are located. This is indicated in FIG. 2 in that the distances between adjacent areas 139 of the B-scans are small in a region 143 of the distal ends 137 compared to regions at greater distances from the distal ends 137.

Figure 3C:
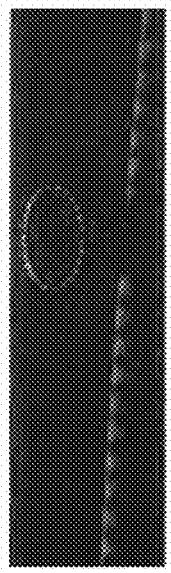
FIGS. 3A-3G show different illustrations of images displayed on a user interface of the surgery system of FIG. 1.
Figure 3E:
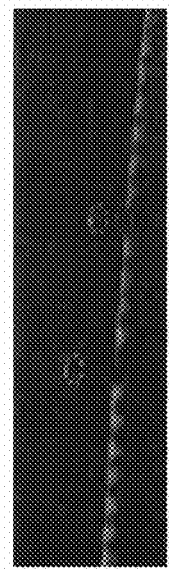
Figure 3G:
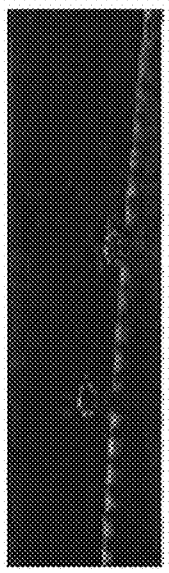
Figure 3B:
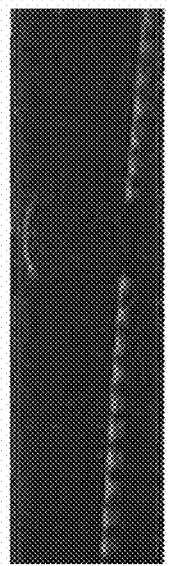
Figure 3D:
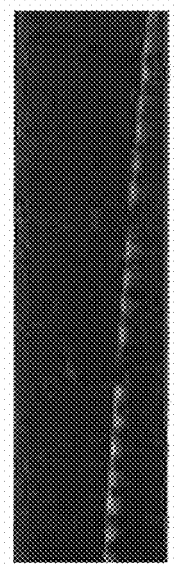
Figure 3F:
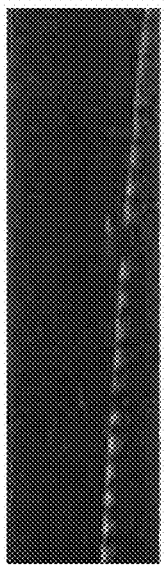
Figure 3A:
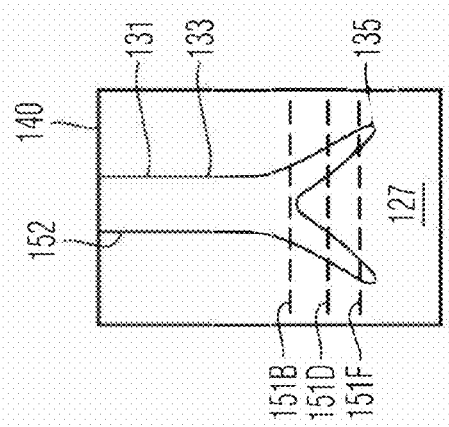

FIG. 3A shows a schematic representation of the camera image 140 obtained by the camera. The camera image 140 represents a top view onto the retina (object 1271 as well as a first portion 152 of the tool 131 disposed before the retina. FIG. 3A further shows the positions of multiple B-scans 139 illustrated by dashed lines 151B, 151D, 151F in FIG. 3A.

FIG. 3B shows an image of the B-scan performed at the positions indicated by a dashed line 151B in FIG. 3A. FIG. 3D shows an image of the B-scan performed at the positions indicated by a dashed line 151D in FIG. 3A. FIG. 3F shows an image of the B-scan performed at the positions indicated by a dashed line 151F in FIG. 3A.

The B-scans of FIGS. 3B, 3D and 3F represent sectional views through the tool 131 and the retina at the different locations indicated by the dashed lines 151B. 151D, 151F. In the B-scan of FIG. 3F, the distal ends 137 of the pair of grippers is located closely to the retina, whereas in the B-scan of FIG. 3D, portions of the gripper 135 disposed at a distance from the distal ends 137 are located a little bit further away from the retina. In the B-scan of FIG. 3B, the shaft 133 of the tool 131 is located yet further away from the surface of the retina.

The images of FIGS. 3B, 3D and 3F are low-contrast, blurry and even experienced surgeons cannot easily interpret these images. For a simplified illustration below, the images of the FIGS. 3A to 3G are schematically reproduced in the FIGS. 4A to 4G.

The shaft 133 of the tool 131 is not fully recognizable in FIG. 3B, as only a surface (i.e., a second portion 1531 disposed upfront in the beam path of the OCT system is identifiable in the depth scans. The remaining part of the surface of the shaft 133 is unidentifiable in the depth scans as the surface shadows the OCT measurement light beam. Hence, the second portion 153 of the tool is recognizable in the image, whereas other portions of the tool are unidentifiable in the image of the B-scan.

Large portions of the retina are recognizable in the image 3B. However, a region 155 of the retina close to the tool 131 and the shaft 133, e.g. opposite to the surface, is unidentifiable in the image of FIG. 3B as also this region 155 is shadowed by the second portion 153 of the tool (shaft) 133.

Hence, it is difficult to exactly estimate the distance between the tool (shaft) 133 and the surface of the retina by observing the depth scans of the OCT system of FIG. 3B.

Therefore, the controller 29 generates images 154 based on the depth scans, wherein portions of the tool and portions of the tissue, e.g. the retina, are clearly visible and complemented in the images 154. The image of FIG. 3C is such an image 154 which is complemented by the controller based on the image of FIG. 3B. The image of FIG. 3E also is such an image 154 which is complemented by the controller based on the image of FIG. 3D, and the image of FIG. 3G also is such an image 154 which is complemented by the controller based on the image of FIG. 3F.

In the image of FIG. 3C, the shaft 133 of the tool is represented by a closed line 156 corresponding to the shaft 133 of the tool 131. The line 156 represents the second portion 153 of the tool and also represents a third portion of the tool indicated by a line 157. The third portion 157 of the tool is unidentifiable in the depth scans of FIG. 3B. Furthermore, the image of FIG. 3C represents a solid line 159 representing the surface of the retina. The line 159 represents the surface of the retina also in the region 155 where the surface of the retina is unidentifiable in the image of FIG. 3B. Due to the complemented portion 157 of the tool 131 and the complemented portion 159 of the surface of the retina, it is possible to precisely estimate the distance d between the tool 131 and the surface of the retina by observing the image of FIG. 3C.

The images of the FIGS. 3E and 3G are complemented with respect to the images of FIGS. 3D and 3F, respectively, in a similar way as previously described for FIG. 3C. Based on these images, it is also possible to precisely estimate the distance between portions of the tool and the surface of the retina. In particular, the distance from the distal ends 137 of the gripper 135 of the tool 131 to the surface of the retina can be estimated precisely based on the complemented image of FIG. 30G which is difficult to impossible from the image of FIG. 3F. From FIG. 3G, it can be seen that the right one of the grippers 135 already touches the surface of the retina, whereas the left one of the grippers is still located at a small distance from the retina. However, from FIG. 3G, it can also be seen that the retina has not yet been deformed by pressure applied to the retina by the right gripper 135.

Therefore, the images of FIGS. 3C, 3E and 3G form a good basis for the surgeon to visually supervise the movements of the surgical tool using these images.

Figure 5:
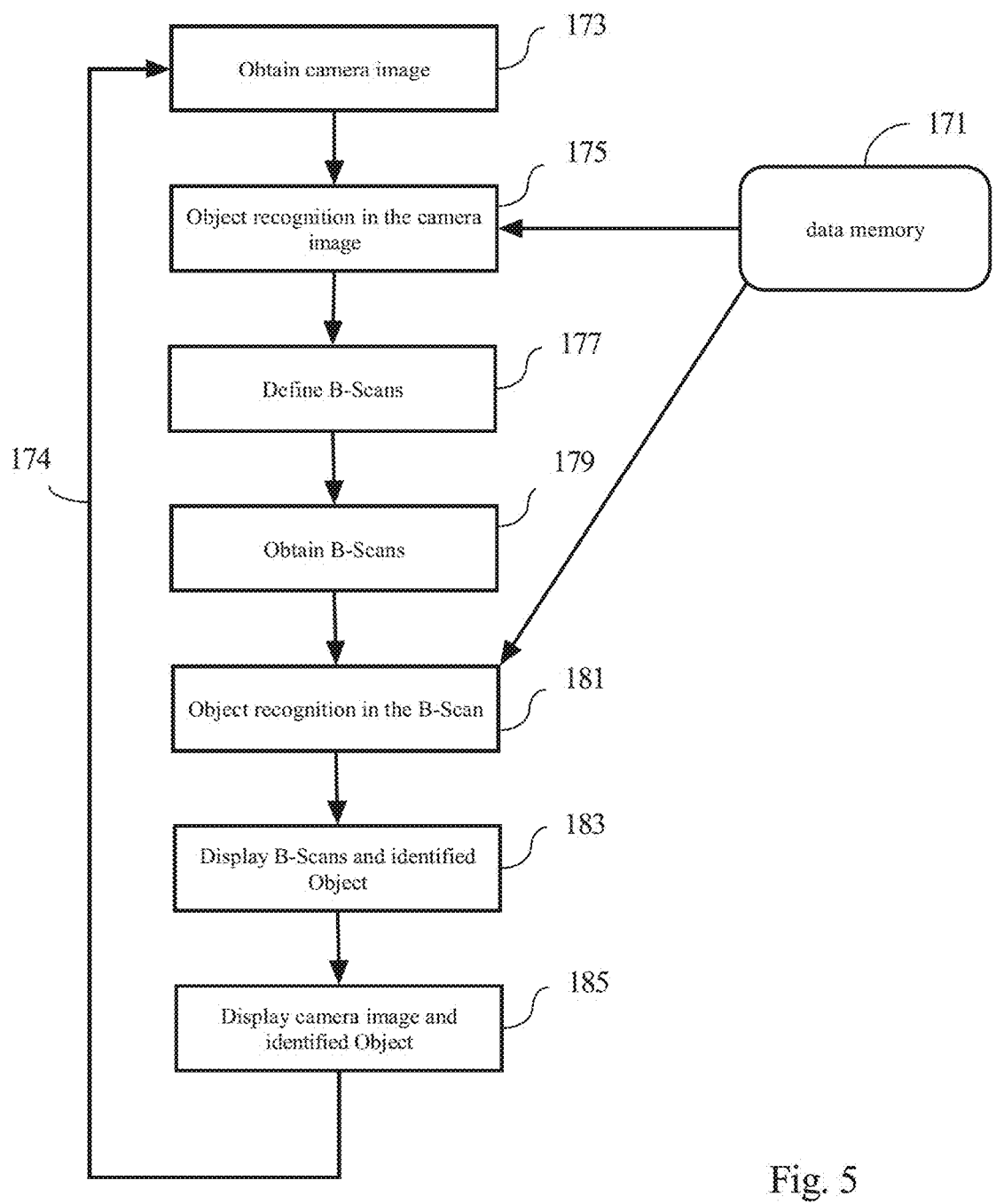
FIG. 5 shows a flowchart illustrating the workflow of the surgery system of FIG. 1.

A workflow of the surgery system for generating the images of FIGS. 3C, 3E and 3G is described in more detail with reference to the flowchart shown in FIG. 5.

Prior to a surgical intervention, geometry data of the surgical tools used for the intervention are stored in a data memory 171. The data memory 171 is connected to the controller 29 by a data wire 172 (see FIG. 1). Herein, seen from the controller 29, the data memory may be an external data base. However, the data memory may also be integrated in the controller 29 and use its working memory.

The approaching of the tool to the retina is tracked by the surgery system. For this, the optics 3 of the surgery system are positioned relative to the retina of the eye so that the region of the retina to be manipulated is disposed in the field of view 7. Then, in step 173, a camera image is obtained. Subsequently, the obtained camera image is analyzed. The step 173 of obtaining the image and the subsequent analysis are repeated in a loop 174 and performed, for example, 15 times per second until the intervention is finished. Analyzing the camera image comprises an object recognition in the camera image, wherein the object recognition is performed using the geometry data of the tools stored in the data memory 171.

The object recognition may use a template-matching-technique, for example. In the template-matching-technique, different templates are generated from the geometry data of a tool, wherein the templates correspond to projections of the tool from different perspectives and orientations. These templates are scaled according to the magnification of the imaging and are correlated with the camera image. When arriving at a sufficiently correlation, it is assumed that the tool is disposed in a location found in the camera image at an orientation corresponding to the generated template. In case the geometry data of multiple different tools are available, templates are generated for all of these tools and a tool present in the image may also be identified based on a template found in the image. Therefore, the identifying of the tool in the camera image comprises determining which one of a plurality of tools is located in the image, determining a position in the field of view where this tool is located and determining an orientation of this tool relative to the field of view.

In step 177, after the object recognition in the camera image in the step 175, the B-scans are defined as described with reference to FIG. 2. The B-scans may be arranged, for example, transverse to a long axis of the tool 131 identified in step 175. The B-scans defined in this way are obtained in step 179 by the OCT system. Then, in step 181, an object recognition on the tool is performed in the B-scans. Then, in step 183, the B-scans as well as the complemented objects are displayed on the monitor 83. In step 185, the complemented tools are displayed on the displays 41 so that the image of the field of view 7 perceivable through the oculars 13 is complemented, too.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. A surgery system comprising:
   a camera and optics, wherein the optics are configured to image a field of view onto the camera, wherein the camera is configured to obtain two-dimensional camera images of the field of view and to generate camera image data representing the camera images;
   an OCT system configured to perform depth scans at selectable locations contained in the field of view and to generate depth scans data representing the depth scans;
   a data memory storing geometry data of at least one surgical tool;
   a controller configured to:
      identify a first portion of the at least one surgical tool in the camera images by object recognition using the geometry data of the at least one surgical tool;
      determine first locations and second locations in the field of view, wherein the at least one surgical tool is located at the first locations and wherein the second locations are located aside of the at least one surgical tool;
      trigger the OCT system to perform first depth scans at the determined first and second locations;
      identify a second portion of the at least one surgical tool in the first depth scans by object recognition using the geometry data of the at least one surgical tool;
      generate a first image representing at least one third portion of the at least one surgical tool, wherein a shape of a representation of the at least one third portion of the at least one surgical tool is extracted from the geometry data and wherein a position of the representation of the at least one third portion of the at least one surgical tool in the generated first image is based on the identified second portion of the at least one surgical tool.

2. The surgery system according to claim 1, wherein the at least one third portion of the at least one surgical tool is unidentifiable in the first depth scans.

3. The surgery system according to claim 1, wherein the controller is further configured to determine the first and second locations based on at least one of the camera images and second depth scans.

4. The surgery system according to claim 1, wherein the generated first image further represents the second portion of the at least one surgical tool, wherein the representation of the second portion of the at least one surgical tool is based on the geometry data and wherein a position of the representation of the second portion of the at least one surgical tool in the generated first image is based on the first depth scans.

5. The surgery system according to claim 1, wherein the generated first image further represents the first depth scans.

6. The surgery system according to claim 5, wherein the first depth scans and the at least one third portion of the at least one surgical tool are represented by different colors in the generated first image; or
   wherein the first depth scans and the second portion of the at least one surgical tool are represented by different colors in the generated first image.

7. The surgery system according to claim 1, wherein the data memory further stores geometry data of at least one anatomic structure,
   wherein the controller is further configured to identify a first portion of the at least one anatomic structure in the depths scans by object recognition using the geometry data of the at least one anatomic structure, and
   wherein the generated first image further represents at least one second portion of the at least one anatomic structure, wherein the representation of the at least one second portion of the at least one anatomic structure is based on the geometry data of the at least one anatomic structure and wherein a position of the representation of the at least one second portion of the at least one anatomic structure in the generated first image is based on the first depth scans.

8. The surgery system according to claim 7, wherein the first depth scans and the at least one second portion of the at least one anatomic structure are represented by different colors in the generated first image.

9. The surgery system according to claim 7, wherein the geometry data of the at least one anatomic structure are geometry data of tissue layers of a retina of an eye.

10. The surgery system according to claim 1, wherein the at least one surgical tool has a distal end, and
    wherein the distal end of the at least one surgical tool is located at the first locations.

11. The surgery system according to claim 10, wherein the controller triggers the OCT system to perform the first depth scans at the first locations at a greater rate compared to those performed at locations which are located at a distance from the distal end of the at least one surgical tool in the field of view.

12. The surgery system according to claim 1, wherein the first locations and the second locations are located at a distance from each other and on at least one line, wherein the at least one surgical tool has a long axis, and wherein the at least one line is orientated either parallel to the long axis or orthogonal to the long axis.

13. The surgery system according to claim 1, wherein the controller comprises a user interface.

14. The surgery system according to claim 13, wherein the user interface comprises a display, and wherein the controller is further configured to display the generated first image on the display.

15. The surgery system according to claim 13, wherein the controller is further configured to generate a second image representing the camera image and one of the first portion and the second portion of the at least one surgical tool.

16. The surgery system according to claim 15, wherein the user interface comprises an ocular, wherein the optics are further configured to image at least a portion of the field of view via the ocular.

17. The surgery system according to claim 16, wherein the controller is further configured to generate a third image representing the first portion and the second portion of the at least one surgical tool and to project the generated second image into a beam path to the ocular.

18. The surgery system according to claim 13, wherein the data memory stores the geometry data of at least three surgical tools,
    wherein the user interface comprises a component configured to obtain a selection of at least one of the at least three surgical tools from a user,
    wherein the geometry data of the at least one selected surgical tool is used by the controller for the object recognition, and wherein the geometry data of the at least one not selected surgical tool is not used by the controller for the object recognition.

19. The surgery system according to claim 1, wherein a beam path of the OCT system traverses optical components of the optics.

* * * * *